US010772703B2

(12) United States Patent
Kralicky

(10) Patent No.: US 10,772,703 B2
(45) Date of Patent: Sep. 15, 2020

(54) METHODS AND APPARATUSES FOR POSITIONING A CAMERA OF A SURGICAL ROBOTIC SYSTEM TO CAPTURE IMAGES INSIDE A BODY CAVITY OF A PATIENT DURING A MEDICAL PROCEDURE

(71) Applicant: TITAN MEDICAL INC., Toronto (CA)

(72) Inventor: Joseph Kralicky, North Kingstown, RI (US)

(73) Assignee: Titan Medical Inc., Toronto (CA)

( * ) Notice: Subject to any disclaimer, the term of this patent is extended or adjusted under 35 U.S.C. 154(b) by 128 days.

(21) Appl. No.: 15/686,571

(22) Filed: Aug. 25, 2017

(65) Prior Publication Data
US 2019/0060029 A1    Feb. 28, 2019

(51) Int. Cl.
*B25J 9/00* (2006.01)
*A61B 90/50* (2016.01)
(Continued)

(52) U.S. Cl.
CPC .............. *A61B 90/50* (2016.02); *A61B 34/30* (2016.02); *A61B 90/361* (2016.02); *B25J 9/1605* (2013.01); *B25J 9/1612* (2013.01); *B25J 9/1664* (2013.01); *B25J 13/02* (2013.01); *B25J 13/04* (2013.01); *B25J 15/0019* (2013.01); *B25J 15/0028* (2013.01); *B25J 15/0066* (2013.01);
(Continued)

(58) Field of Classification Search
CPC ....... H03L 7/00; G01R 13/0254; H03K 5/159
See application file for complete search history.

(56) References Cited

U.S. PATENT DOCUMENTS

| 6,926,709 B2 | 8/2005 | Bieger et al. |
| 7,890,211 B2 * | 2/2011 | Green ................ A61B 1/00193 700/251 |

(Continued)

FOREIGN PATENT DOCUMENTS

| EP | 2 687 186 A1 | 1/2014 |
| WO | WO 00/60521 A1 | 10/2000 |

(Continued)

OTHER PUBLICATIONS

International Search Report and Written Opinion in Application No. PCT/US2018/045646, dated Oct. 23, 2018 in 12 pages.

(Continued)

*Primary Examiner* — Ian Jen
(74) *Attorney, Agent, or Firm* — Knobbe, Martens, Olson & Bear, LLP

(57) ABSTRACT

Methods and apparatuses for positioning a camera of a surgical robotic system to capture images inside a body cavity of a patient during a medical procedure are disclosed. In some embodiments, the method involves receiving location information at a controller of a surgical robotic system performing the medical procedure, the location information defining a location of at least one tool with respect to a body cavity frame of reference, and in response to receiving an align command signal at the controller, causing the controller to produce positioning signals operable to cause the camera to be positioned within the body cavity frame of reference to capture images of the at least one tool for display to an operator of the surgical robotic system.

24 Claims, 9 Drawing Sheets

(51) Int. Cl.
  *A61B 90/00* (2016.01)
  *B25J 15/00* (2006.01)
  *B25J 9/16* (2006.01)
  *B25J 13/02* (2006.01)
  *B25J 13/04* (2006.01)
  *A61B 34/30* (2016.01)
  *A61B 34/00* (2016.01)

(52) U.S. Cl.
  CPC .............. *A61B 34/71* (2016.02); *A61B 90/37* (2016.02); *A61B 2034/301* (2016.02); *A61B 2090/371* (2016.02)

(56) References Cited

U.S. PATENT DOCUMENTS

| | | | |
|---|---|---|---|
| 8,108,072 B2 | 1/2012 | Zhao et al. | |
| 8,147,503 B2 | 4/2012 | Zhao et al. | |
| 8,600,551 B2* | 12/2013 | Itkowitz | G09B 23/285 700/245 |
| 9,108,318 B2 | 8/2015 | Diolaiti | |
| 9,333,042 B2 | 5/2016 | Diolaiti et al. | |
| 2002/0111713 A1* | 8/2002 | Wang | A61B 34/70 700/245 |
| 2005/0222554 A1 | 10/2005 | Wallace et al. | |
| 2009/0088634 A1 | 4/2009 | Zhao et al. | |
| 2010/0274087 A1* | 10/2010 | Diolaiti | A61B 34/37 600/118 |
| 2010/0332031 A1* | 12/2010 | Itkowitz | B25J 9/1689 700/245 |
| 2012/0059391 A1* | 3/2012 | Diolaiti | A61B 34/37 606/130 |
| 2012/0071892 A1* | 3/2012 | Itkowitz | A61B 34/35 606/130 |
| 2013/0331644 A1 | 12/2013 | Pandya et al. | |
| 2014/0276951 A1* | 9/2014 | Hourtash | A61B 34/30 606/130 |
| 2014/0343416 A1* | 11/2014 | Panescu | A61B 34/30 600/431 |
| 2019/0314095 A1 | 10/2019 | Unsworth | |

FOREIGN PATENT DOCUMENTS

| | | |
|---|---|---|
| WO | WO 2010/039394 A1 | 4/2010 |
| WO | WO 2015/031777 A1 | 3/2015 |
| WO | WO 2015/135057 A1 | 9/2015 |
| WO | WO 2019/040278 | 2/2019 |

OTHER PUBLICATIONS

International Preliminary Report on Patentability received in co-pending International Application No. PCT/US2018/045646, dated Feb. 25, 2020, in 6 pages.

* cited by examiner

METHODS AND APPARATUSES FOR POSITIONING A CAMERA OF A SURGICAL ROBOTIC SYSTEM TO CAPTURE IMAGES INSIDE A BODY CAVITY OF A PATIENT DURING A MEDICAL PROCEDURE

BACKGROUND

1. Field

This disclosure relates to a surgical robotic systems and more particularly to positioning a camera to capture images inside a body cavity of a patient during a medical procedure.

2. Description of Related Art

Miniaturized cameras are used during investigative medical procedures and surgical procedures such as laparoscopic surgery to produce images of a site of the procedure within a body cavity of the patient. The camera generally has a field of view that captures only a portion of the body cavity of the patient and may have a positioning mechanism for orienting the camera to change the portion of the body cavity within the field of view.

SUMMARY

In accordance with one disclosed aspect there is provided a method for positioning a camera to capture images inside a body cavity of a patient during a medical procedure. The method involves receiving location information at a controller of a surgical system performing the medical procedure, the location information defining a location of at least one tool with respect to a body cavity frame of reference, and in response to receiving an align command signal at the controller, causing the controller to produce positioning signals operable to cause the camera to be positioned within the body cavity frame of reference to capture images of the at least one tool for display to an operator of the surgical system.

Movement of the at least one tool within the body cavity may be caused by movement signals produced by the controller based on kinematic calculations and receiving location information may involve using results of the kinematic calculations to determine the location of the at least one tool.

The method may involve receiving location signals at the controller, the location signals being indicative of an actual location of the at least one tool within the body cavity frame of reference.

Causing the controller to produce positioning signals may involve causing the controller to produce positioning signals operable to cause the camera to be positioned such that a field of view of the camera is disposed to cause a reference point associated with the at least one tool to be centered within the captured images.

The reference point may involve a point on the at least one tool proximate a distal end of the at least one tool.

Receiving location information may involve receiving location information defining locations of a plurality of tools with respect to a body cavity frame of reference, and the reference point may include a point disposed in-between respective distal ends of the plurality of tools.

The method may involve receiving operator input of a desired offset between the reference point and the center of the field of view of the camera and causing the controller to produce positioning signals may involve causing the controller to produce positioning signals operable to cause the camera to be positioned such that a field of view of the camera is disposed offset from the reference point by the desired offset within the captured images.

The method of may further involve, while the align command signal is being received at the controller and in response to receiving operator input from an input device configured to generate input signals for controlling movement of the at least one tool, causing the controller to continue to produce movement signals for causing movement of the at least one tool while simultaneously producing camera positioning signals operable to cause the camera to follow the at least one tool within the body cavity frame of reference.

Receiving the align command signal may involve causing the controller to determine whether a camera align control has been activated by the operator.

The camera align control may involve one or more of a finger actuated switch and a foot actuated switch.

Receiving the align command signal may involve causing the controller to determine whether at least one of a pattern of movement of the at least one tool has been received at an input device configured to generate input signals for controlling movement of the at least one tool, and a pattern of movement of an end effector disposed at a distal tip of the at least one tool has been received from an input device configured to generate input signals for controlling movement of the end effector.

Receiving the align command signal may involve causing the controller to determine whether at least one of a reference point associated with the at least one tool is disposed outside of a defined central region within the captured image, and a reference point associated with a currently active one of a plurality of tools is disposed outside of a defined central region within the captured image.

In accordance with another disclosed aspect there is provided an apparatus for positioning a camera to capture images inside a body cavity of a patient during a medical procedure performed by a surgical system. The apparatus includes a controller operably configured to receive location information, the location information defining a location of at least one tool with respect to a body cavity frame of reference. The controller is configured to produce positioning signals operable to cause the camera to be positioned within the body cavity frame of reference to capture images of the at least one tool for display to an operator of the surgical system in response to receiving an align command signal.

Movement of the at least one tool within the body cavity may be caused by movement signals produced by the controller based on kinematic calculations and the controller may be configured to receive location information by using results of the kinematic calculations to determine the location of the at least one tool.

The controller may be configured to receive location signals, the location signals being indicative of an actual location of the at least one tool within the body cavity frame of reference.

The controller may be configured to produce positioning signals operable to cause the camera to be positioned such that a field of view of the camera is disposed to cause a reference point associated with the at least one tool to be centered within the captured images.

The reference point may include a point on the at least one tool proximate a distal end of the at least one tool.

The controller may be configured to receive location information defining locations of a plurality of tools with respect to a body cavity frame of reference, and the reference point may include a point disposed in-between respective distal ends of the plurality of tools.

The controller may be configured to receive operator input of a desired offset between the reference point and the center of the field of view of the camera and the controller may be further configured to cause the camera to be positioned such that a field of view of the camera is disposed offset from the reference point by the desired offset within the captured images.

While the align command signal is being received at the controller and while receiving operator input from an input device configured to generate input signals for controlling movement of the at least one tool, the controller may be configured to continue to produce movement signals for causing movement of the at least one tool while simultaneously producing camera positioning signals operable to cause the camera to follow the at least one tool within the body cavity frame of reference.

The align command signal may be produced in response to determining that a camera align control has been activated by the operator.

The camera align control may include one or more of a finger actuated switch and a foot actuated switch.

The align command signal may be produced in response to the controller determining whether at least one of a pattern of movement of the at least one tool has been received at an input device configured to generate input signals for controlling movement of the at least one tool, and a pattern of movement of an end effector disposed at a distal tip of the at least one tool has been received from an input device configured to generate input signals for controlling movement of the end effector.

The align command signal may be produced by the controller when at least one of a reference point associated with the at least one tool is disposed outside of a defined central region within the captured image, and a reference point associated with a currently active one of a plurality of tools is disposed outside of a defined central region within the captured image.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
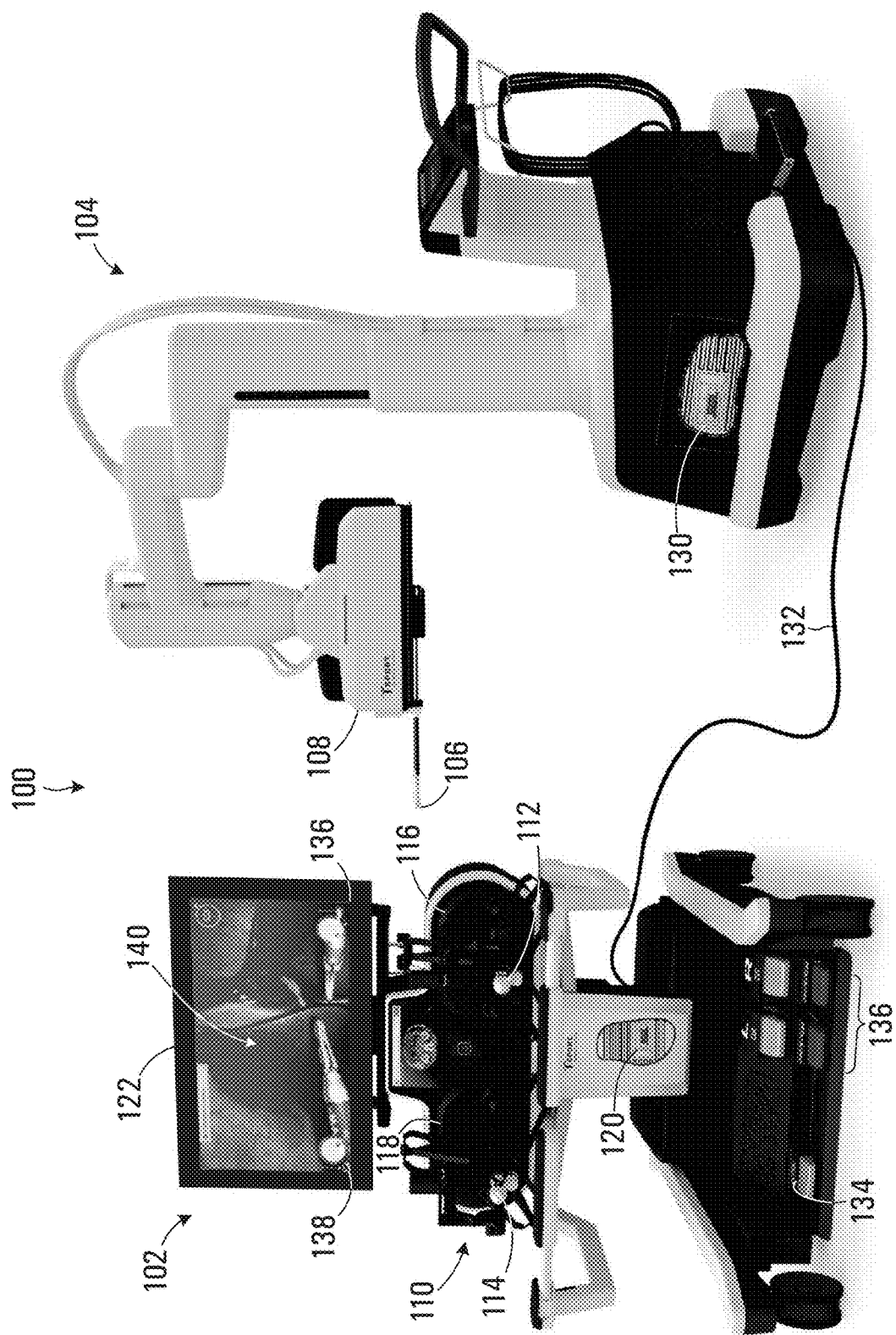
FIG. 1 is a perspective view of a robotic surgery system according to some embodiments.

Referring to FIG. 1, a robotic surgery system is shown generally at 100. According to some embodiments, the system 100 includes a workstation 102 and an instrument cart 104. The instrument cart 104 includes at least one instrument 106 mounted on a moveable drive unit 108 that houses an instrument drive for manipulating the instrument. The workstation 102 includes an input device 110 for use by a surgeon for controlling the instrument 106 via the instrument drive to perform surgical operations on a patient. The input device 110 may be implemented using a haptic interface available from Force Dimension, of Switzerland, for example.

Figure 2:
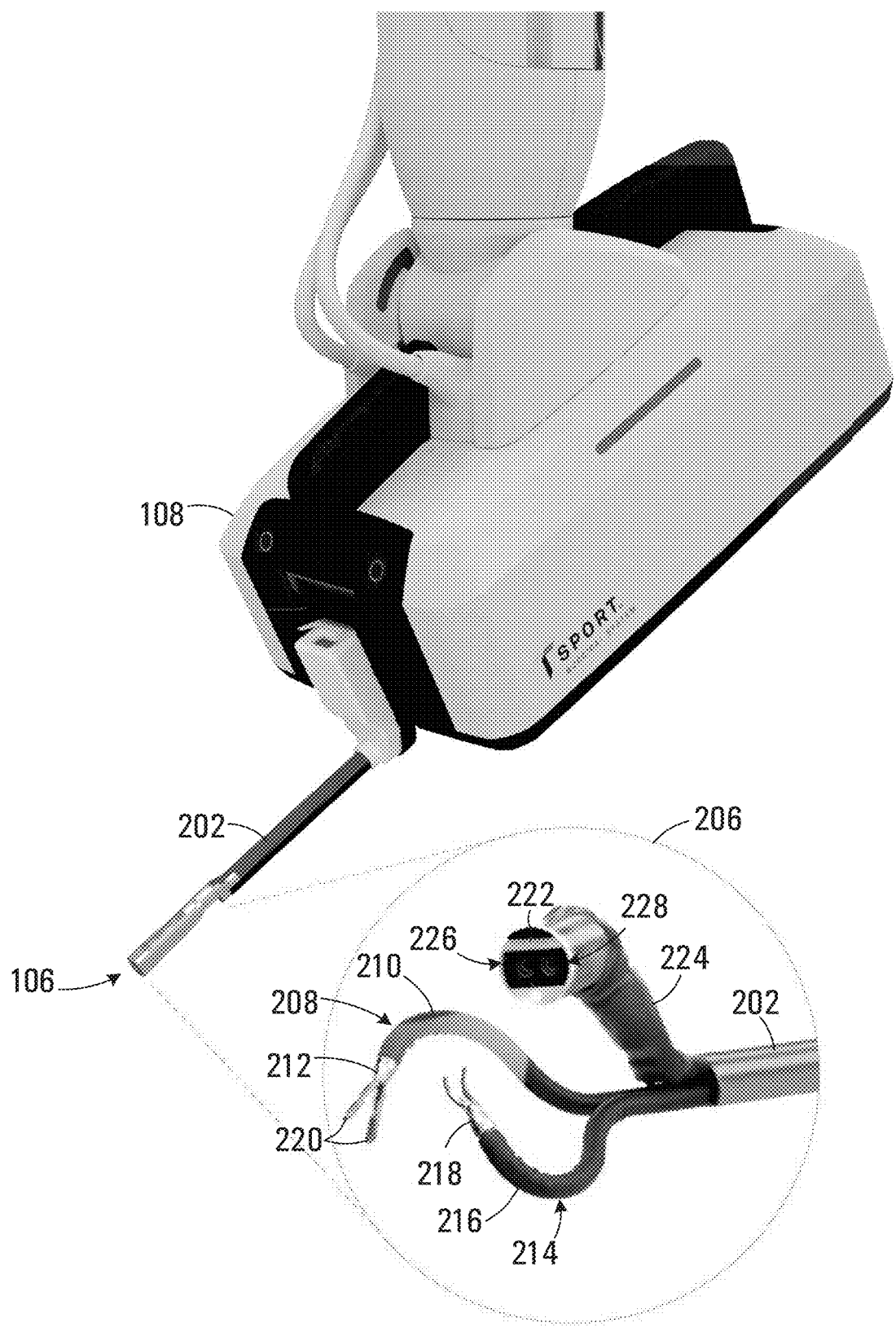
FIG. 2 is a perspective view of a drive unit of the robotic surgery system shown in FIG. 1 according to some embodiments.

The instrument 106 and the drive unit 108 are shown in more detail in FIG. 2. Referring to FIG. 2, in some embodiments, the instrument 106 includes an insertion tube 202 that is inserted through an incision in a wall of the patient's abdomen or other body cavity to provide access to a surgical workspace within the body cavity. Once inserted into the surgical workspace, the camera 222 on the instrument 106 is deployed as shown in the insert 206 in FIG. 2. In this embodiment the instrument 106 accommodates a right side tool 208 having a manipulator 210 and an end effector 212, and a left side tool 214 having a manipulator 216 and an end effector 218. The right side tool 208 and left side tool 214 are driven by associated tool drives (not shown).

In the embodiment shown the end effector 212 is a pair of forceps having opposing moveable gripper jaws 220 controlled by the associated tool drive for manipulating tissue, while the end effector 218 is a pair of curved dissecting forceps controlled by the associated tool drive for also manipulating tissue. The instrument 106 also includes a camera 222 deployed on an articulated arm 224 that is able to pan, elevate, and tilt the camera. In this embodiment the camera 222 includes a pair of spaced apart image sensors 226 and 228 for producing stereoscopic views of the surgical workspace. The camera 222 is initially positioned in-line with the insertion tube 202 prior to insertion through the incision and then deployed as shown at 206. The tools 208 and 214 are also initially positioned in-line with the insertion tube 202 prior to installation and insertion through the insertion tube and then deployed as shown at 206.

Figure 3:
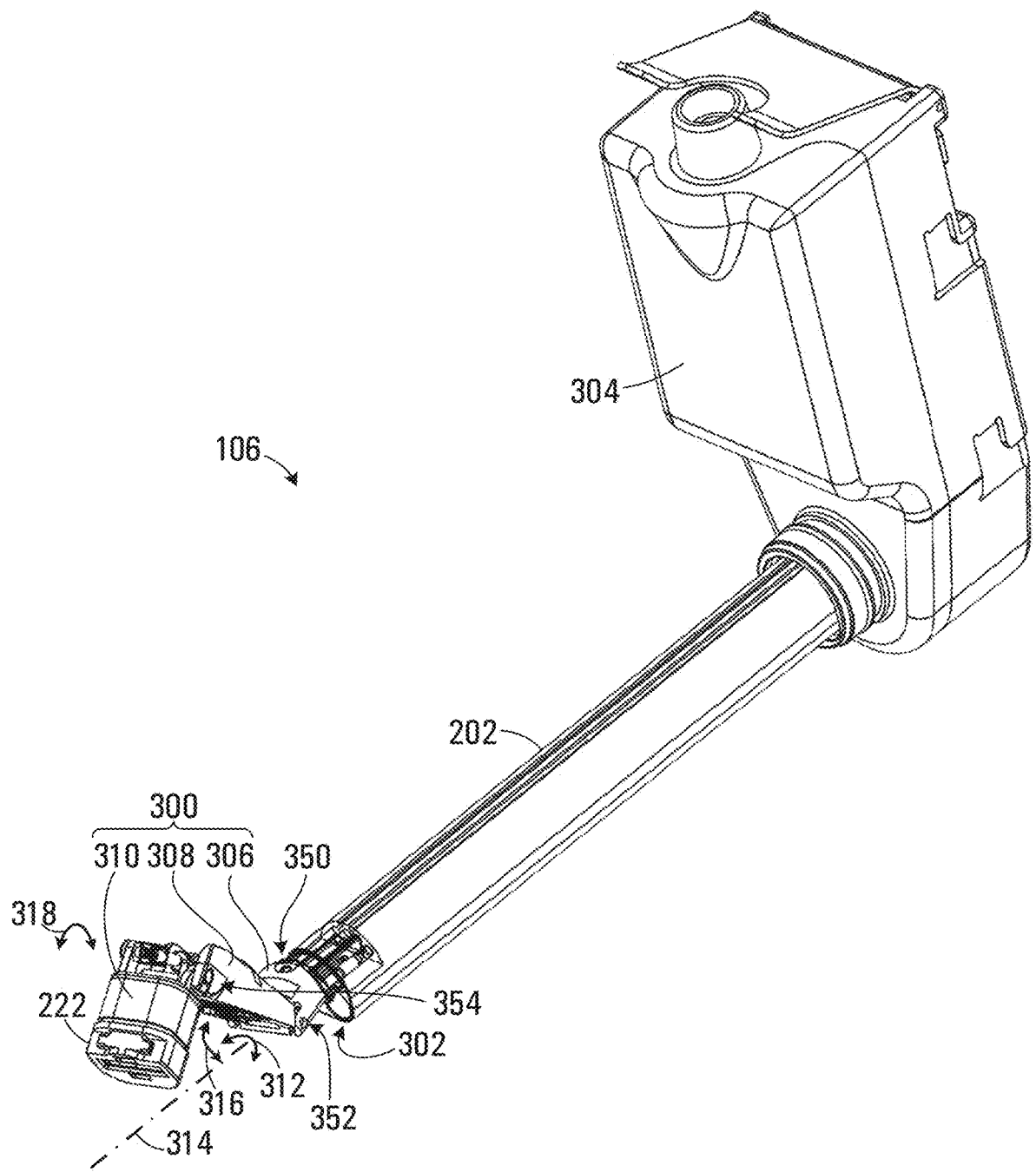
FIG. 3 is a perspective view of an instrument used in the robotic surgery system of FIG. 1 according to some embodiments.

The instrument 106 without the tools 208 and 214 installed is shown in more detail in FIG. 3. Referring to FIG. 3, in some embodiments, the camera 222 is mounted at a distal end of a plurality of connected linkages 300 extending from a distal end 302 of the insertion tube 202. The insertion tube 202 extends outwardly from a drive interface 304 that is removably received on the drive unit 108 (shown in FIG. 2). The plurality of connected linkages 300 include a panning linkage 306 connected to the distal end 302 of the insertion tube 202 via a first revolute joint 350, an elevating linkage 308 connected to the panning linkage via a second revolute joint 352, and a tilt linkage 310 (i.e. the housing of the camera 222) connected to the elevating linkage via a third revolute joint 354. The first revolute joint 350 constrains of the panning linkage 306 to side-to-side motion in the direction indicated by the arrow 312. The second revolute joint 322 constrains the elevating linkage 308 to movement away from a longitudinal axis 314 in the direction indicated by the arrow 316. The third revolute joint 324 constrains the tilt linkage 310 to movement for tilting the camera 222 forward and backward with respect to the longitudinal axis 142 in the direction indicated by the arrow 318. In other embodiments the plurality of connected linkages 300 may be otherwise arranged and one or more of the linkages may be omitted.

Movement of the plurality of connected linkages 300 is actuated by drivers (not shown) housed within the drive unit 108 (shown in FIG. 2) cause the drive interface 304 to actuate the respective panning, elevation, and tilt movements of the instrument 106 to position the camera 222. The drive interface 304 and drive unit 108 are described in more detail in commonly owned PCT patent application PCT/CA2017/000078 entitled "CAMERA POSITIONING METHOD AND APPARATUS FOR CAPTURING IMAGES DURING A MEDICAL PROCEDURE" filed on Apr. 4, 2017, which is incorporated herein by reference in its entirety.

Referring back to FIG. 1, the input device 110 includes a right input device 116 for controlling the right instrument 208 and a left input device 118 for controlling the left tool 214. The right input device 116 includes a right hand controller 112 and the left input device 118 includes a left hand controller 114, the hand controllers being mechanically coupled to the respective input devices.

The workstation 102 also includes a workstation processor circuit 120, which is in communication with the input devices 116 and 118 and the hand controllers 112 and 114 for receiving input from a surgeon. The instrument cart 104 also includes an instrument processor circuit 130 for controlling the instrument 106. The workstation processor circuit 120 and instrument processor circuit 130 act as controllers for controlling operations of the system 100. In this embodiment the instrument processor circuit 130 is in communication with the workstation processor circuit 120 via an interface cable 132 for transmitting signals between the workstation processor circuit 120 and the instrument processor circuit 130. In other embodiments communication between the workstation processor circuit 120 and the processor circuit 130 may be wireless or via a computer network, and the workstation 102 and may even be located remotely from the instrument cart 104.

The workstation 102 also includes a display 122 in communication with the workstation processor circuit 120 for displaying real time images and/or other graphical depictions of the surgical workspace. In this embodiment where the camera 222 includes the pair of spaced apart image sensors 226 and 228, the display 122 is configured to provide separate 2D stereoscopic views of the surgical workspace that provide a 3D depth effect when viewed through suitable stereoscopic spectacles worn by the surgeon.

The workstation 102 also includes a footswitch 134, which is actuable by the surgeon to provide an enablement signal to the workstation processor circuit 120. The 102 also includes a plurality of footswitches 136, which are actuable by the right foot of the surgeon and provide input signals to the workstation processor circuit 120 for controlling the instrument 106.

Input signals are generated by the left and right input devices 116 and 118 in response to movement of the hand controllers 112 and 114 by a surgeon within an input device workspace associated with the left and right input devices. The manipulators 210 and 216 associated with the tools 208 and 214 spatially position the end effectors 212 and 218 of the respective tools 208 and 214 in the surgical workspace in response to the input signals.

Figure 4:
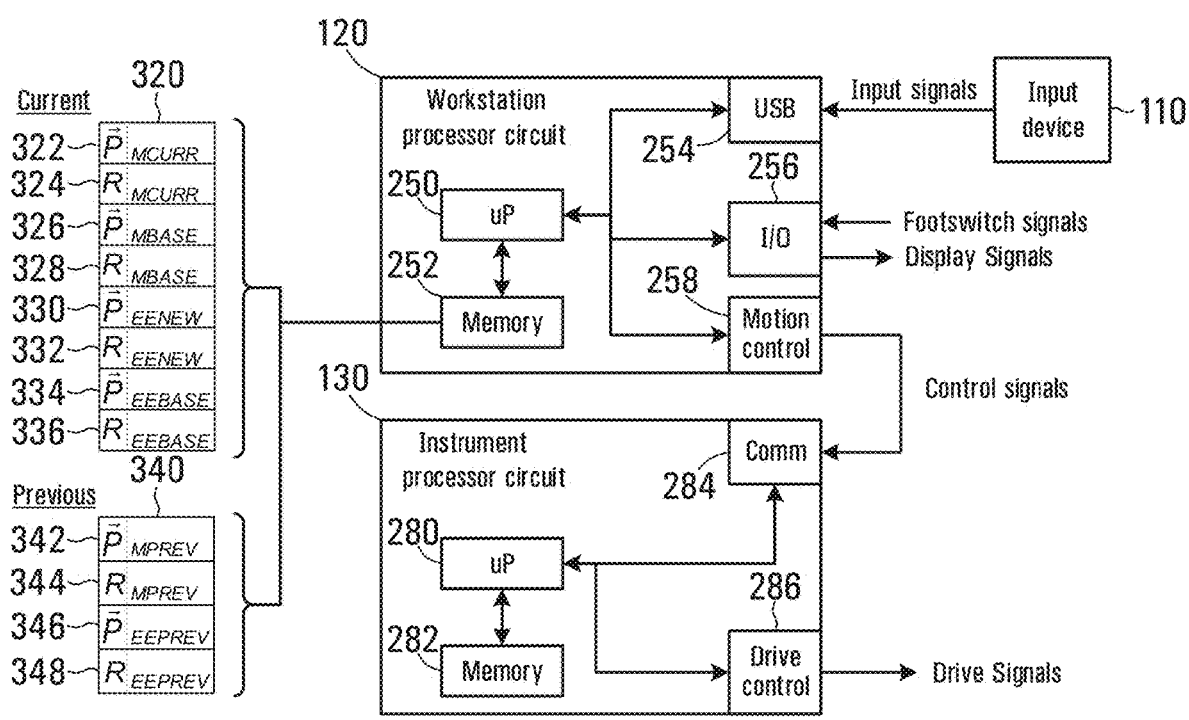
FIG. 4 is a block diagram of the processor circuit elements of the robotic surgery system shown in FIG. 1 according to some embodiments.

A block diagram of the processor circuit elements of the system 100 is shown in FIG. 4. Referring to FIG. 4, in some embodiments, the workstation processor circuit 120 includes a microprocessor 250. The workstation processor circuit 120 also includes a workstation memory 252, a USB interface 254, an input/output 256 and a motion control interface 258, all of which are in communication with the microprocessor 250. The input/output 256 includes an input for receiving an enablement signal from the footswitch 134 and an output for producing display signals for driving the display 122.

In this embodiment the input device 110 communicates using a USB protocol and the USB interface 254 receives input signals produced by the input device in response to movements of the hand controllers 112 and 114. The microprocessor 250 processes the input signals based on a current mapping between the input device workspace and the surgical workspace and causes the motion control interface 258 to transmit control signals, which are conveyed to the instrument processor circuit 130 via the interface cable 132. The mapping may include a scale factor that scales movements in input device workspace to produce scaled movements in surgical workspace. For example a 100 mm translation in input device workspace may be scaled by a scale factor of 0.5 to produce a 50 mm movement in surgical workspace for fine movement.

The workstation processor circuit 120 receives the footswitch signals at the input/output 256 from the footswitch 134 and the plurality of footswitches 136. The workstation memory 252 includes a current buffer 320 and a previous buffer 340 including a plurality of stores for storing values associated with the control signals, as described later herein.

The instrument processor circuit 130 includes a microprocessor 280, a memory 282, a communications interface 284, and a drive control interface 286, all of which are in communication with the microprocessor.

The microprocessor 280 receives the input signals at the communications interface 284. The microprocessor 280 processes the control signals and causes the drive control interface 286 to produce drive signals for moving the tools 208 and 214.

The workstation processor circuit 120 thus acts as a master subsystem for receiving user input, while the instrument processor circuit 130 and tools 208 and 214 act as a slave subsystem in responding to the user input.

Figure 5:
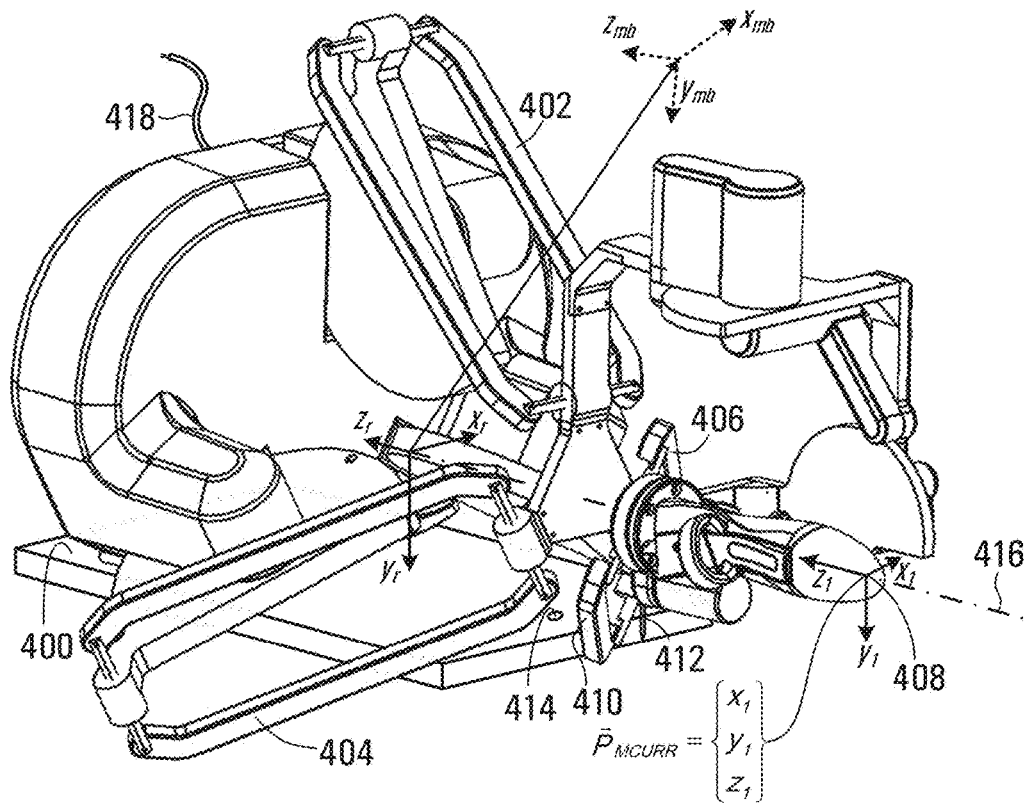
FIG. 5 is a perspective view of a right input device of the robotic surgery system shown in FIG. 1 according to some embodiments.

The right input device 116 is shown in greater detail in FIG. 5. For simplicity, only the right input device 116 will be further described, it being understood that left input device 118 operates in the same way. In some embodiments, the input device 116 is supported on a base 400 and includes arms 402, 404, and 406.

The right hand controller 112 is mounted to the arms 402-406 to permit positioning and rotation about orthogonal axes $x_1$, $y_1$ and $z_1$ of a Cartesian reference frame. The Cartesian reference frame has an origin at a point on a body of the hand controller 112 and the location of the origin defines the hand controller position 408 (i.e. at the origin). In this embodiment, the hand controller 112 is mounted on a gimbal mount 410. The arms 402-406 confine movements of the hand controller 112 and hence the hand controller position 408 to within the hemispherical input device workspace. In one embodiment the input device 116 may also be configured to generate haptic forces for providing haptic feedback to the hand controller 112 through the arms 402-406 and gimbal mount 410.

The input device 116 has sensors (not shown) that sense the position of each of the arms 402-406 and rotation of the hand controller 112 about each of the $x_1$, $y_1$ and $z_1$ axes and produces signals representing the position of the hand controller in the workspace and the rotational orientation of hand controller relative to an input device Cartesian reference frame $x_r$, $y_r$, $z_r$. In this embodiment, the position and orientation signals are transmitted as input signals via a USB connection 418 to the USB interface 254 of the workstation processor circuit 120.

In this embodiment, the gimbal mount 410 has a pin 412 extending downwardly from the mount and the base 400 includes a calibration opening 414 for receiving the pin. When the pin 412 is received in the opening 414 the input device 116 is located in a calibration position that is defined relative to the input device Cartesian reference frame $x_r$, $y_r$, $z_r$. The input device reference frame has an $x_r$-$z_r$ plane parallel to the base 400 and a $y_r$ axis perpendicular to the base. The $z_r$ axis is parallel to the base 400 and is coincident with an axis 416 passing centrally through the input device 116.

The input device 116 produces current hand controller signals and current hand controller orientation signals that represent the current position and orientation of the hand controller 112. The signals may be represented by a current hand controller position vector and a current hand controller rotation matrix. The current hand controller position vector is given by:

$$\vec{P}_{MCURR} = \begin{Bmatrix} x_1 \\ y_1 \\ z_1 \end{Bmatrix},$$

where $x_1$, $y_1$, and $z_1$ represent coordinates of the hand controller position 408 (i.e. the origin of the coordinate system $x_1$, $y_1$, $z_1$) relative to the input device reference frame $x_r$, $y_r$, $z_r$. The current hand controller rotation matrix is given by:

$$R_{MCURR} = \begin{bmatrix} x_{1x} & y_{1x} & z_{1x} \\ x_{1y} & y_{1y} & z_{1y} \\ x_{1z} & y_{1z} & z_{1z} \end{bmatrix},$$

where the columns of the matrix represent the axes of the hand controller reference frame $x_1$, $y_1$, $z_1$ relative to the input device reference frame $x_r$, $y_r$, $z_r$. The matrix $R_{MCURR}$ thus defines the current rotational orientation of the hand controller 112 relative to the $x_r$, $y_r$, and $z_r$ fixed master reference frame. The current hand controller position vector $\vec{P}_{MCURR}$ and current handle rotation matrix $R_{MCURR}$ are transmitted as current hand controller position and current hand controller orientation signals via the USB connection 418 to the USB interface 254 of the workstation processor circuit 120. The workstation processor circuit 120 stores the three values representing the current handle position vector $\vec{P}_{MCURR}$ in a store 322 and the nine values representing the current hand controller rotation matrix $R_{MCURR}$ in a store 324 of the current buffer 320 of workstation memory 252.

Figure 6:
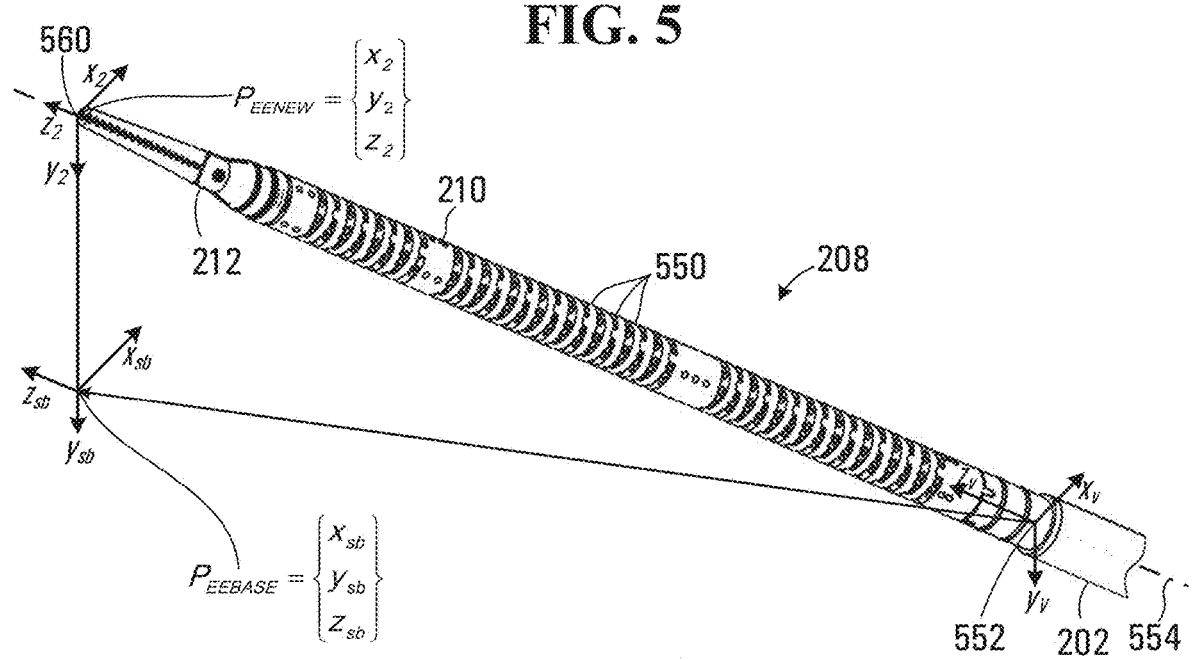
FIG. 6 is a perspective view of a right side tool of the robotic surgery system shown in FIG. 1 according to some embodiments.

The right side tool 208 is shown in greater detail in FIG. 6. Referring to FIG. 6, in some embodiments, the manipulator 210 is configured to position the end effector 212 within the surgical workspace by activating various drivers in the drive unit 108 in response to the drive signals produced by the drive control interface 286 of the tool processor circuit 130. The drive signals are produced by the drive control interface 286 in response to the control signals received at the communications interface 284 from the workstation processor circuit 120 and are based on the current hand controller position vector $\vec{P}_{MCURR}$ and current hand controller rotation matrix $R_{MCURR}$ stored in the stores 322 and 324 of the current buffer 320 in the workstation memory 252.

The tool 208 includes a plurality of the identical "vertebra" 550 as described in commonly owned PCT patent application PCT/CA2013/001076 entitled "ARTICULATED TOOL POSITIONER AND SYSTEM EMPLOYING SAME" filed on Dec. 20, 2013, which is incorporated herein by reference in its entirety. The vertebra 550 are operable to move with respect to each other when control wires passing through the vertebra are extended or retracted to cause movements of the manipulator 210. The position and orientation of the end effector 212 is defined relative to a fixed slave reference frame having axes $x_v$, $y_v$, and $z_v$, which intersect at a point referred to as the fixed slave reference position 652. The fixed slave reference position 552 lies on a longitudinal axis 554 of the tool 208 and is contained in a plane perpendicular to the longitudinal axis and containing a distal edge of the insertion tube 202. In one embodiment the fixed slave reference frame acts as a body cavity frame of reference.

In the embodiment shown, the gripper jaws 220 of the end effector 212 are positioned and oriented within an end effector workspace. A tip of the gripper jaws 220 may be designated as an end effector position 560 defined as the origin of an end effector Cartesian reference frame $x_2$, $y_2$, $z_2$. The end effector position 560 is defined relative to the slave reference position 552 and the end effector may be positioned and orientated relative to the fixed slave reference frame $x_v$, $y_v$, $z_v$ for causing movement of the manipulator 210 and/or the end effector 212.

The current hand controller position signal $\vec{P}_{MCURR}$ and current hand controller orientation signal $R_{MCURR}$ cause movement of the end effector 212 of the tool 208 to new end effector positions and desired new end effector orientations and are represented by a new end effector position vector $\vec{P}_{EENEW}$:

$$P_{EENEW} = \begin{Bmatrix} x_2 \\ y_2 \\ z_2 \end{Bmatrix},$$

where $x_2$, $y_2$, and $z_2$ represent coordinates of the end effector position 560 within the end effector workspace relative to the $x_v$, $y_v$, $z_v$ fixed slave reference frame, and a 3×3 end effector rotation matrix $R_{EENEW}$:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the columns of the $R_{EENEW}$ matrix represent the axes of the end effector reference frame $x_2$, $y_2$, and $z_2$ written in the fixed slave reference frame $x_v$, $y_v$, and $z_v$. $R_{EENEW}$ thus defines a new orientation of the end effector 212 in the end effector workspace, relative to the $x_v$, $y_v$, and $z_v$ fixed slave reference frame. Values for the vector $\vec{P}_{EENEW}$ and rotation matrix $R_{EENEW}$ are calculated as described later herein and stored in stores 330 and 332 of the current buffer 320 of the workstation memory 252 respectively.

When the system 100 initially starts up, the workstation processor circuit 120 sets a master base position vector $\vec{P}_{MBASE}$ equal to the current hand controller vector $\vec{P}_{MCURR}$ and causes a definable master base rotation matrix $R_{MBASE}$ to define an orientation that is the same as the current orientation defined by the hand controller rotation matrix $R_{MCURR}$ associated with the current hand controller rotation. At startup the following operations are therefore performed:

$$\vec{P}_{MBASE} = \vec{P}_{MCURR}, \text{ and}$$

$$R_{MBASE} = R_{MCURR}.$$

For the example of the right tool 208, the hand controller 112 reference frame represented by the axes $x_1$, $y_1$, and $z_1$ shown in FIG. 5 and the definable master base reference frame represented by the axes $x_{mb}$, $y_{mb}$, and $z_{mb}$ (also shown in FIG. 5) thus coincide at startup of the system 100. Referring back to FIG. 4, the workstation processor circuit 120 stores the values representing the definable master base position vector $\vec{P}_{MBASE}$ and the definable master base rotation matrix $R_{MBASE}$ in the stores 326 and 328 of the current buffer 320 of the workstation memory 252.

At startup of the system 100 there would be no previously stored values for the new end effector position vector $\vec{P}_{EENEW}$ and the new end effector rotation matrix $R_{EENEW}$ and in one embodiment these values are set to home configuration values. A home configuration may be defined that produces a generally straight manipulator 210 for the tool 208 as shown in FIG. 6 and the values of $\vec{P}_{PEENEW}$ and $R_{EENEW}$ for the home configuration may be preconfigured at initialization. On startup of the system 100 the workstation processor circuit 120 also causes a definable end effector base position vector $\vec{P}_{EEBASE}$ and a definable end effector base rotation matrix $R_{EEBASE}$ to be set to the home configuration values of $\vec{P}_{EENEW}$ and $R_{EENEW}$. Additionally, values for $\vec{P}_{EEPREV}$ and $R_{EEPREV}$ stored in the stores 346 and 348 of the previous buffer 340 (shown in FIG. 4) of the workstation processor circuit 120 are also set to the home configuration values of $\vec{P}_{EENEW}$ and $R_{EENEW}$. In other embodiments, the home configuration may define configuration variables to produce different bent or both straight and bent tool positioning device poses for the home configuration.

At startup, the following operations are therefore performed:

$$\vec{P}_{EEBASE} = \vec{P}_{EENEW} = \vec{P}_{EEPREV}, \text{ and}$$

$$R_{EEBASE} = R_{EENEW} = R_{EEPREV}.$$

The end effector reference frame represented by the axes $x_2$, $y_2$, and $z_2$ shown in FIG. 6 and the definable slave base reference frame represented by the axes $x_{sb}$, $y_{sb}$, and $z_{sb}$ thus coincide at startup of the system 100. Referring back to FIG. 4, the workstation processor circuit 120 stores the values $x_{sb}$, $y_{sb}$, and $z_{sb}$ representing the definable slave base position vector $\vec{P}_{EEBASE}$ in store 334 and stores the values representing the definable slave base rotation matrix $R_{MBASE}$ in a store 336 of the current buffer 320 of the workstation memory 252.

Figure 7:
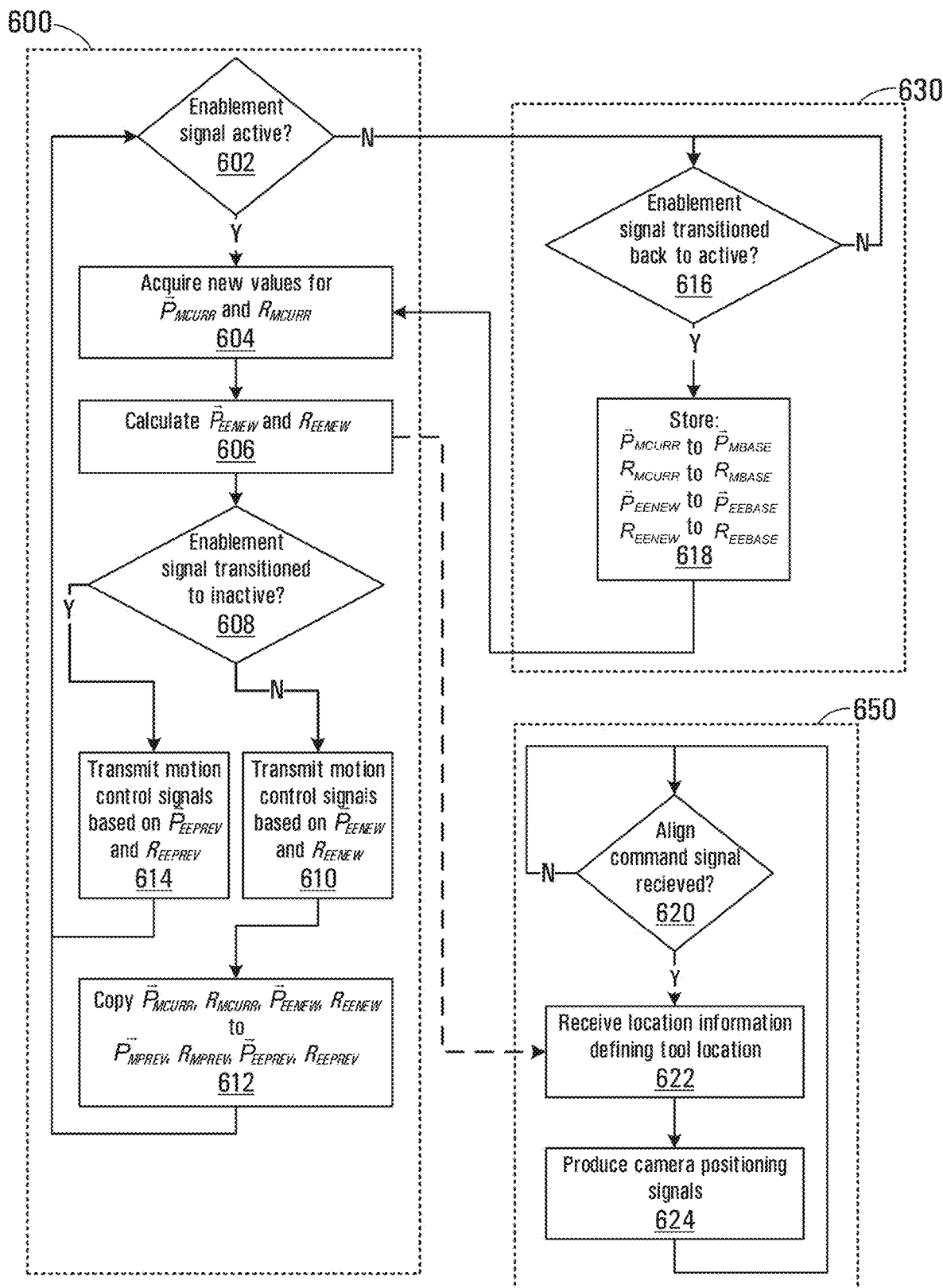
FIG. 7 is a process flowchart depicting blocks of code for directing the processor circuit elements shown on FIG. 4 to control operation of the robotic surgery system shown in FIG. 1 according to some embodiments.

Referring to FIG. 7, in some embodiments, a flowchart depicting blocks of code for directing the workstation processor circuit 120 to execute a process for moving the instrument 106 is shown generally at 600. A flowchart depicting blocks of code for directing the workstation processor circuit 120 to execute a base setting process is shown generally at 600 and a flowchart depicting blocks of code for directing the workstation processor circuit 120 to execute a process for positioning the camera 222 to capture images inside the body cavity of the patient is shown generally at 650. In the embodiment shown the processes 600, 630, and 650 are simultaneously executed by the microprocessor 250 in parallel. The blocks generally represent codes that direct the microprocessor 250 to perform various functions. The actual code to implement each block may be written in any suitable program language, such as C, C++, C #, Java, OpenGL, and/or assembly code, for example.

The movement process 600 begins at block 602, which directs the microprocessor 250 to determine whether the enablement signal produced by the footswitch 134 is in an active state. If at block 602, it is determined that the footswitch 134 is currently released, the enablement signal will be in the active state and the microprocessor is directed to block 604, which directs the microprocessor 250 to read new values for $\vec{P}_{MCURR}$ and $R_{MCURR}$ from the current buffer 320 of the workstation memory 252, which represent the current hand controller position vector $\vec{P}_{MCURR}$ and current hand controller matrix $R_{MCURR}$. Block 606 then directs the microprocessor 250 to calculate new end effector position signals $\vec{P}_{EENEW}$ and new end effector orientation signals $R_{EENEW}$ representing a desired end effector position 560 and desired end effector orientation, relative to the fixed slave reference position 552 and the slave base orientation (shown in FIG. 6). Block 606 also directs the microprocessor 250 to store values representing the new end effector position vector $\vec{P}_{EENEW}$ in the store 330 and to store values representing the desired end effector orientation matrix $R_{EENEW}$ in the store 332 of the current buffer 320 of the workstation memory 252.

The new end effector position signals $\vec{P}_{EENEW}$ and new end effector orientation signals $R_{EENEW}$ are calculated according to the following relations:

$$\vec{P}_{EENEW} = A(\vec{P}_{MCURR} - \vec{P}_{MBASE}) + \vec{P}_{EEBASE} \qquad \text{Eqn 1a}$$

$$R_{EENEW} = R_{EEBASE} R_{MBASE}^{-1} R_{MCURR} \qquad \text{Eqn 1b}$$

where:

$\vec{P}_{EENEW}$ is the new end effector position vector that represents the new desired position of the end effector 212 in the end effector workspace, and is defined relative to the slave base reference position;

A is a scalar value representing a scaling factor in translational motion between the hand controller 112 (master) and the tool 208 (slave);

$\vec{P}_{MCURR}$ is the current representation of the hand controller position vector stored in the store 322 of the current buffer 320, the hand controller position vector being defined relative to the fixed master reference frame $x_r$, $y_r$, and $z_r$;

$\vec{P}_{MBASE}$ is the last-saved position vector $\vec{P}_{MCURR}$ for the hand controller 112 that was shifted at the last transition of the enablement signal from the inactive state to the active state or on system initialization or by operation of a control interface by an operator;

$\vec{P}_{EEBASE}$ is the last saved position vector $\vec{P}_{EENEW}$ for the end effector 212 that was shifted at the last transition of the enablement signal from the inactive state to the active state or on system initialization;

$R_{EENEW}$ is the new end effector orientation matrix representing the current orientation of the end effector 212, and is defined relative to the fixed slave reference position 552;

$R_{EEBASE}$ is the last-saved rotation matrix $R_{EENEw}$ of the end effector 212 shifted at the last transition of the enablement signal from the inactive state to the active state;

$R_{MBASE}^{-1}$ is the inverse of rotation matrix $R_{MBASE}$, which is the last-saved rotation matrix $R_{MCURR}$ of the hand controller 112 saved at the last transition of the enablement signal from the inactive state to the active state; and $R_{MCURR}$ is the currently acquired rotation matrix representing the orientation of hand controller 112 relative to the fixed master reference frame $x_r$, $y_r$, and $z_r$.

Block 608 then directs the microprocessor 250 to determine whether the enablement signal has transitioned to the inactive state. If the enablement signal has not transitioned to the inactive state at block 608, block 610 then directs the microprocessor 250 to cause the motion control interface 258 to transmit control signals based on the newly calculated values for $\vec{P}_{EENEW}$ and $R_{EENEW}$. When the control signals are received at the communications interface 284 of the instrument processor circuit 130, the microprocessor 280 causes drive signals to be produced to cause the end effector 212 to assume a position and orientation determined by the current position and current orientation of the hand controller 112.

Block 612 then directs the microprocessor 250 to copy the current position vector $\vec{P}_{MCURR}$ and the current rotation matrix $R_{MCURR}$ stored in stores 322 and 324 of the current buffer 320 into stores 342 ($\vec{P}_{MPREV}$) and 344 ($R_{MPREV}$) of the previous buffer 340 of the workstation memory 252. Block 612 also directs the microprocessor 250 to copy the newly calculated end effector position vector $\vec{P}_{EENEW}$ and the newly calculated end effector rotation matrix $R_{EENEW}$ into stores 346 and 348 of the previous buffer 340. By storing the newly calculated end effector position vector $\vec{P}_{EENEW}$ and newly calculated end effector rotation matrix $R_{EENEW}$, as previously calculated end effector position vector $\vec{P}_{EEPREV}$ and previously calculated end effector rotation matrix $R_{EEPREV}$, a subsequently acquired new end effector position vector $\vec{P}_{EENEW}$ and subsequently acquired new end effector rotation matrix $R_{EENEW}$ can be calculated from the next received hand controller position vector $\vec{P}_{MCURR}$ and next received hand controller rotation matrix $R_{MCURR}$ provided by the input device 116.

If at block 608, the enablement signal has transitioned to the inactive state, the microprocessor 250 is directed to block 614. Block 614 directs the microprocessor 250 to cause the motion control interface 258 to transmit control signals based on the previously calculated values of $\vec{P}_{EEPREV}$ and $R_{EEPREV}$ in the respective stores 346 and 348 of the previous butter 340 of the workstation memory 252. The control signals transmitted by the motion control interface 258 are thus derived from the last saved values of $\vec{P}_{EENEW}$ and $R_{EENEW}$. The instrument processor circuit 130 receives the control signals and produces drive signals at the drive control interface 286 that inhibit further movement of the tool 208

If at block 602, it is determined that the footswitch 134 is currently depressed, the enablement signal will be in the inactive state and the microprocessor is directed to block 616 initiating the base setting process 630. The base setting process 630 (blocks 616 and 618) is executed asynchronously whenever the enablement signal produced by the footswitch 134 transitions from the active state to the inactive state. During the base setting process 630, the drive signals are maintained at the values that were in effect at the time the enablement signal transitioned to inactive at block 608. At block 616 the microprocessor 250 is directed to determine whether the enablement signal has transitioned back to being in the active state. While enablement signal remains inactive (i.e. while the footswitch 134 is depressed) the control signals transmitted by the motion control interface 258 are based only on the previously calculated end effector position and previously calculated orientation signals $\vec{P}_{EEPREV}$ and $R_{EEPREV}$ that were in effect before the enablement signal transitioned to inactive. If at block 616 the enablement signal remains in the inactive state, the microprocessor 250 is directed to repeat block 616 and the process is thus effectively suspended while the enablement signal remains in in the inactive state. While the footswitch 134 is depressed, the surgeon may thus move the hand controller 112 to a new location to relocate the input device workspace relative to the surgical workspace.

When at block 616 the enablement signal transitions from the inactive state to the active state, the microprocessor 250 is directed to block 618. Block 618 directs the microprocessor 250 to set new base positions and orientations for the hand controller 112 and end effector 212 respectively. Block 618 directs the microprocessor 250 to cause current values of current hand controller position vector $\vec{P}_{MCURR}$ and the hand controller rotation matrix $R_{MCURR}$ to be stored in locations 326 and 328 of the current buffer 320 workstation memory 252 as new values for the master base position vector $\vec{P}_{MBASE}$ and master base rotation matrix $R_{MBASE}$. Block 618 also directs the microprocessor 250 to cause current values for the end effector position signal $\vec{P}_{EENEW}$ and the end effector orientation signal $R_{EENEW}$ to be stored in stores 334 and 336 of the current buffer 320 as the definable end effector base position vector $\vec{P}_{EEBASE}$ and definable slave base rotation matrix $R_{MBASE}$. Following execution of block 618, the microprocessor 250 is directed back to block 604 of the process 600, which directs the microprocessor to permit further movement of the tool 208. The control signals transmitted by the motion control interface 258 thus cause the instrument processor circuit 130 to produce drive signals at the drive control interface 286 that cause further movement of the tool 208.

The base setting process 630 thus allows the tool 208 to be immobilized by depressing the footswitch 134 while the hand controller 112 of the input device 116 is moved to a new location. When the footswitch 134 is released, control of the tool 208 resumes at the new position of the hand controller 112. The hand controller 112 may thus be repositioned as desired while the tool remains immobile, allowing a greater workspace to the surgeon and preventing unintended movements that may inflict injury to the patient.

The camera align process 650 begins at block 620, which directs the microprocessor 250 to determine whether an align command signal has been received. The align command signal may be generated by any of the input devices 116 and 118, the hand controllers 112 and 114, the footswitches 136, or other input received from the surgeon at the workstation 102. The align command signal may be generated when a camera align control has been activated by the operator. For example, in one embodiment the align command signal may be generated in response to actuation of an input button by a finger of the operator on either of the hand controllers 112 and 114 and detected in the input signals received from the input device 110. Alternatively, the align command signal may be generated by a secondary input device such as a touch screen or through the actuation of one or more of the footswitches 136 and detected in the footswitch signals received at the input/output 256. In the embodiment where a touch screen is used, an image of the surgical site may be displayed where the user can touch the area whereas to align the camera by generating the align command signal. In other embodiments the align command signal may be generated in response to a pre-defined or user defined input such as a specific movement of the hand controllers 112 and 114. If an align command signal is not received the microprocessor 250 is directed to repeat block 620 and the process 650 is thus effectively suspended waiting for the align command signal to transition to an active state.

In other embodiments the align command signal may be produced by causing the workstation processor circuit 120 to determine whether a pattern of movement of the tool or tools 208 and 214 has been received. For example, the hand controllers 112 and 114 may be moved in a pre-determined pattern, or the end effectors 212 and 218 may be moved toward each other to touch, or some other pattern of movement may be defined to cause generation of the align command signal. In response to detecting the pattern of movement, the workstation processor circuit 120 may cause the align command signal to be placed in the active state until another defined pattern of movement is detected.

In yet another embodiment, the align command signal may be set to the active state when the workstation processor circuit 120 determines that a reference point associated with either the tool 208 or 214 is disposed outside of a defined central region within the captured image. The reference point may be associated with either of the tools 208 or 214, or may be associated with a currently active tool.

If an align command signal is received by the microprocessor 250, block 620 directs the microprocessor to receive location information defining the location of either or both of the tools 208 and 214. The location information is provided by the simultaneous execution of block 606 of the process 600 and may be retrieved from the stored values of the calculated end effector position vector $\vec{P}_{EENEW}$ and calculated end effector rotation matrix $R_{EENEW}$ in the stores 330 and 332 of the current buffer 320 of the workstation processor circuit 120 shown in FIG. 4. In this embodiment movement of the tool 208 and/or 214 within the body cavity is be caused by movement signals produced by the instrument processor circuit 130 based on kinematic calculations on the inputs produced by the input device 110 and results of the kinematic calculations are thus used to determine the location of the tool. In other embodiments the system 100 may include a location system (not shown) that generates location signals representing an actual location of either or both tools 208 and 214, and the location signals may be received at the workstation processor circuit 120 and used to determine the location of the tool.

The process 650 then continues at block 624, which directs the microprocessor 250 to produce camera positioning signals operable to cause the camera 222 to be positioned within the body cavity frame of reference (i.e. $x_v$, $y_v$, $z_v$) to capture images. For the instrument 106 shown in FIG. 3, the positioning signals are generated for controlling each of the plurality of connected linkages 300 to move the camera 222 to be positioned such that a field of view of the camera is disposed to capture images of a portion of the body cavity with respect to the location of the tool or tools 208 and 214. For example, in one embodiment the camera 222 may be moved to cause a reference point associated with the tools to be centered within the captured images. The reference point may be a point on the tool proximate a distal end, such as one of the end effectors 212 or 218, or the gripper jaws 220 of the tool 208, or any other reference point. Alternatively, location information may be received for each of the tools 208 and 214 and the reference point may be a point disposed in-between respective distal ends of the tools. In some embodiments, operator input of a desired offset between the reference point and the center of the field of view of the camera may be received or otherwise determined and positioning signals may be produced to cause the camera 222 to be positioned such that a field of view is disposed to offset the reference point by the desired offset within the captured images.

Block 624 then directs the microprocessor 250 back to block 620 to determine whether the align command signal is still in the active state. As an example, if the align command signal is produced in response to actuation of one of the footswitches 134 or 136 and the footswitch is still being depressed, then blocks 622 and 624 are repeated. Accordingly, if the tool location has changed, block 622 causes the microprocessor 250 to retrieve the new location and block 624 generates updated camera positioning signals for positioning the camera 222. Blocks 622 and 624 thus cause the workstation processor circuit 120 to produce camera positioning signals that will cause the camera to follow the tool 208 within the body cavity frame of reference (i.e. $x_v$, $y_v$, $z_v$) while the align command signal is active.

If at block 620, the align command signal is not received or is no longer in the active state, the camera 222 remains in the position corresponding to the camera positioning signals last generated at block 556. The process 650 is run concurrently with other processes being executed by the microprocessor 250 and may be repeated at a fixed time interval during operation of the system 100. For example, in one embodiment the process 500 may be executed several times per second so that movement of the camera 222 while the align command signal is being generated is sufficiently smooth to prevent image jitter in the images displayed on the display 122.

The end effector position vector $\vec{P}_{EENEW}$ or $\vec{P}_{EEPREV}$ and end effector orientation matrix $R_{EENEW}$ or $R_{EEPREV}$ respectively produced at blocks 606 and 614 provide a desired location end effector tip 660 (shown in FIG. 6) with respect to the fixed slave reference position 652. In embodiment shown in FIG. 4, the microprocessor 250 of the workstation processor circuit 120 causes the motion control interface 258 to transmit motion control signals that define a pose required by the positioning manipulator 210 to position and orient the end effector 212 in the desired end effector position and orientation. The motion control signals are thus generated based on a kinematic configuration of the manipulator 210 and end effector 212 to place the end effector position 660 at a desired position and orientation.

Figure 8:
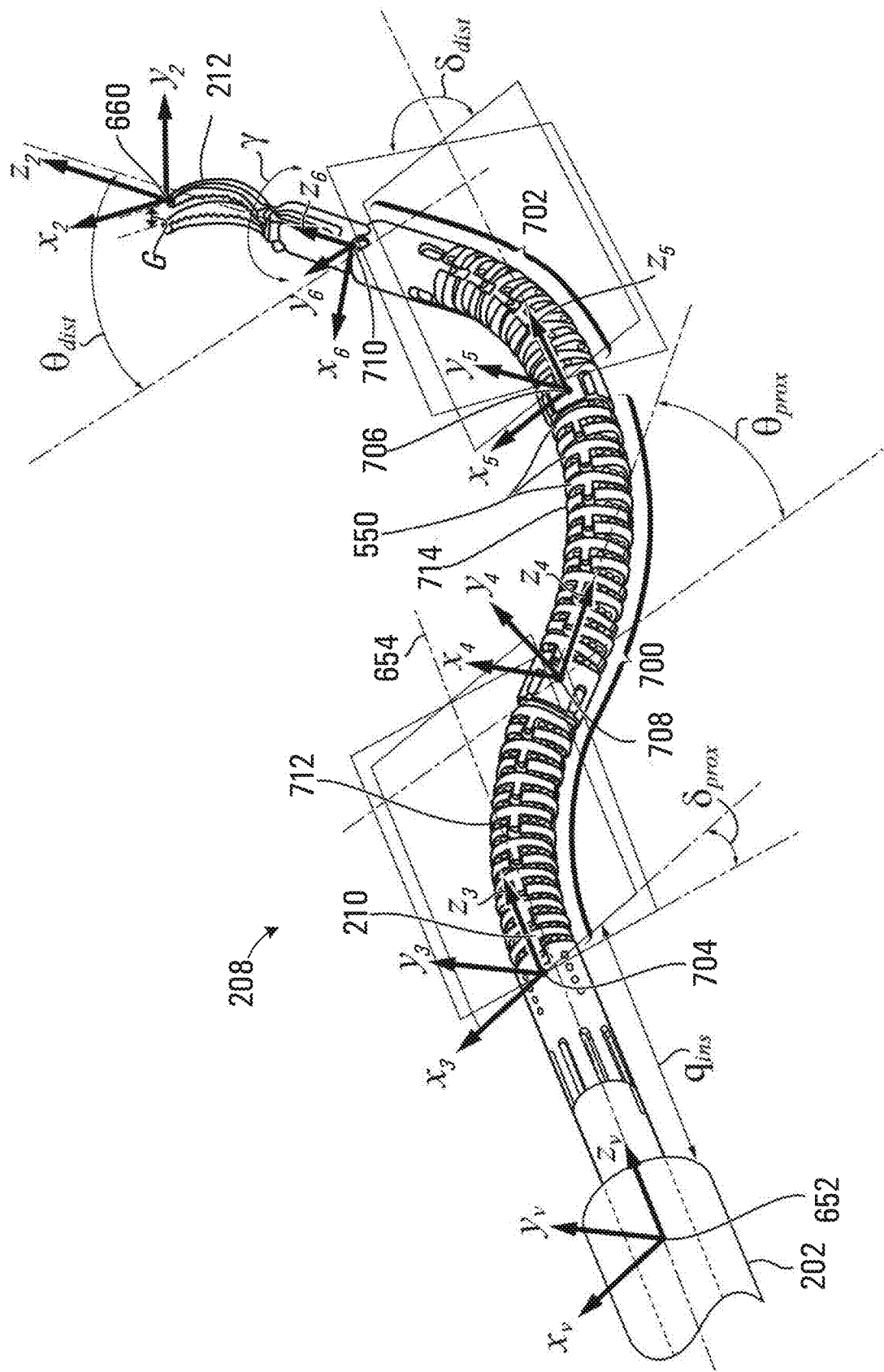
FIG. 8 is a side perspective view of the right side tool in a bent pose according to some embodiments.
Figure 9:
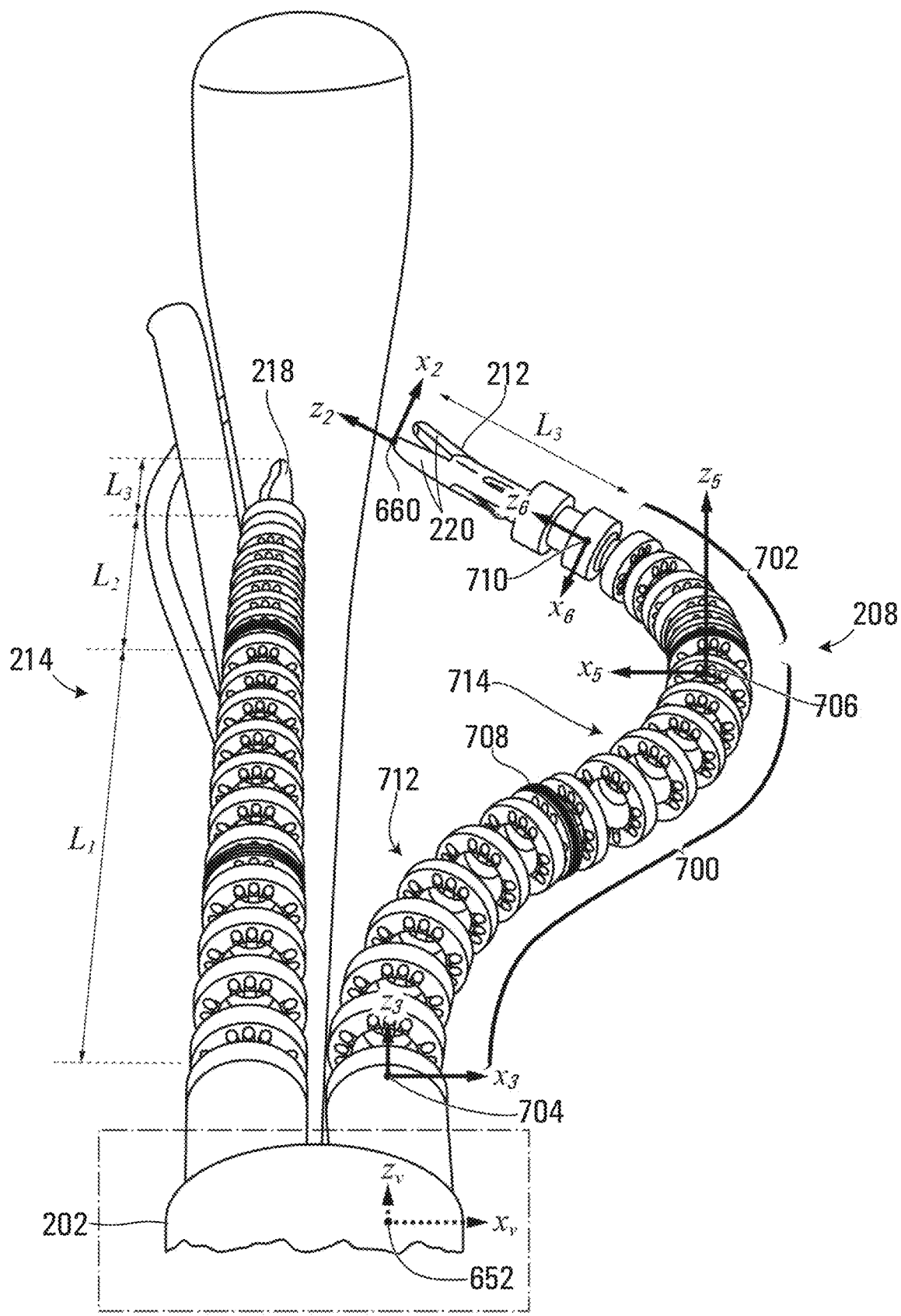
FIG. 9 is a rear perspective view of the left and right side tools according to some embodiments.

Generation of motion control signals by the instrument processor circuit 130 is described with further reference to FIG. 8 and FIG. 9. According to some embodiments, the right side tool 208 in a bent pose is shown from a side perspective in FIG. 8 and from a rear prospective in FIG. 9. The left side tool 214 is also shown in FIG. 9 in a straight pose corresponding to the home configuration described above. Referring to FIG. 8 and FIG. 9, the manipulator 210 of the tool 208 has a first articulated segment referred to as an s-segment 700 and a second articulated segment referred to as a distal segment 702. The segments each include the plurality of vertebra 550. The s-segment 700 begins at a distance from the insertion tube 202, referred to as the insertion distance $q_{ins}$, which is a distance between the fixed slave reference position 652 defined at the origin of the slave fixed base reference frame $x_v$, $y_v$, and $z_v$ and a first position 704 at an origin of a first position reference frame $x_3$, $y_3$, and $z_3$. The insertion distance $q_{ins}$ represents an unbendable portion of the manipulator 210 that extends out of the end of the insertion tube 202. In the embodiment shown, the insertion distance $q_{ins}$ may be about 10-20 mm, while in other embodiments the insertion distance may be longer or shorter, varying from 0-100 mm, for example.

The s-segment 700 extends from the first position 704 to a third position 706 defined as an origin of a third reference frame having axes $x_5$, $y_5$, and $z_5$ and is capable of assuming a smooth s-shape when control wires (not shown) inside the s-segment 700 are pushed and pulled. The s-segment 700 has a mid-point at a second position 708, defined as the origin of a second position reference frame having axes $x_4$, $y_4$, and $z_4$. The s-segment 700 has a length $L_1$, best shown in FIG. 9 for the left side tool manipulator 216. In the embodiment shown, the length $L_1$ may be about 65 mm.

The distal segment 702 extends from the third position 706 to a fourth position 710 defined as an origin of a fourth reference frame having axes $x_6$, $y_6$, and $z_6$. The distal segment 702 has a length $L_2$, best shown in FIG. 9 for the left side tool manipulator 216. In the embodiment shown, the length $L_2$ may be about 30 mm.

Each end effector 212 and 218 also has an end effector length, which in the embodiment shown is a gripper length $L_3$ extending from the fourth position 710 to the end effector tip position 660 defined as the origin of the axes $x_2$, $y_2$, and $z_2$. The gripper length $L_3$ is best shown in FIG. 9 again for the left side tool manipulator 216 and in one embodiment may be about 25 mm. The slave reference position 652, first position 704, second position 708, third position 706, fourth position 710, and the end effector position 660 may collectively be referred to as tool reference positions.

As described in PCT/CA2013/001076, by pushing and pulling on control wires inside the manipulators 210 and 216, the s-segments 700 of the manipulators may be bent into various degrees of an s-shape, from the straight condition shown in FIG. 8 to a partial s-shape for the right side tool 208 shown in FIG. 8 and FIG. 9 to a full s-shape. The s-segment 700 is sectional in that it has a first section 712 and a second section 714 on opposite sides of the second position 708. Referring to FIG. 8, the first and second sections 712 and 714 lie in a first bend plane containing the first position 704, second position 708, and third position 706. The first bend plane is at an angle $\delta_{prox}$ to the $x_v$-$z_v$ plane of the fixed slave reference frame $x_v$, and $z_v$. The first section 712 and second section 714 are bent in the first bend plane through opposite but equal angles $\vartheta_{prox}$ such that no matter the angle $\vartheta_{prox}$ or the bend plane angle $\delta_{prox}$, the $z_5$ axis of the third position 706 is always parallel to and aligned in the same direction as the $z_v$ axis of the fixed slave reference position 652. Thus, by pushing and pulling on the control wires within the manipulator 210, the third position 706 can be placed at any of a number of discrete positions in space within a cylindrical volume about the first position 704. This cylindrical volume may be referred to as the s-segment workspace.

In addition, the distal segment 702 lies in a second bend plane containing the third position 706 and the fourth position 710. The second bend plane is at an angle $\delta_{dist}$ to the $x_v$-$z_v$ plane of the fixed slave reference frame $x_v$, $y_v$, and $z_v$. The distal segment 702 is bent in the second bend plane at an angle $\vartheta_{dist}$. Thus, by pushing and pulling the control wires within the manipulator 210, the fourth position 710 can be placed within another volume in space about the fourth position 710. This volume may be referred to as the distal workspace. The combination of the s-segment workspace and the distal workspace may be referred to as the positioning device workspace as this represents the total possible movement of the tool 208 as effected by the manipulator 210. The left side tool 214 may be similarly positioned by the manipulator 216.

The distance between the fourth position 710 and the end effector position 660 is the distance between the movable portion of the distal segment 702 and the tip of the gripper 220 of the end effector 212 in the embodiment shown, i.e. the length the gripper length $L_3$ shown in FIG. 9. Generally, a portion of the gripper between the fourth position 710 and the end effector position 660 will be unbendable.

In the embodiment shown, the end effector 212 include moveable gripper jaws 220 that are rotatable about the $z_2$ axis in the $x_2$-$y_2$ plane of the end effector reference frame, the angle of rotation being represented by an angle γ relative to the positive $x_2$ axis. Finally, the gripper jaws 220 may be at any of varying degrees of openness from fully closed to fully open (as limited by a hinge joint of the jaws). The varying degrees of openness may be defined as "G". In summary therefore, the motion control signals are generated based on a kinematic configuration of the manipulator 210 and end effector 212 as defined by the following configuration variables:

$q_{ins}$ represents a distance from the slave reference position 652 defined by axes $x_v$, $y_v$, and $z_v$ to the first position 704 defined by axes $x_3$, $y_3$ and $z_3$ where the s-segment 700 of the manipulator 210 begins;

$\delta_{prox}$ represents a first bend plane in which the s-segment 700 is bent relative to the $x_v$-$y_v$ plane of the fixed slave reference frame;

$\vartheta_{prox}$ represents an angle at which the first and second sections 712 and 714 of the s-segment 700 are bent in the first bend plane;

$\delta_{dist}$ represents a second bend plane in which the distal segment 702 is bent relative to the $x_v$-$y_v$ plane of the fixed slave reference frame;

$\theta_{dist}$ represents an angle through which the distal segment 702 is bent in the second bend;

γ represents a rotation of the end effector 212 about axis $z_2$; and

G: represents a degree of openness of the gripper jaws 220 of the end effector 212 (this is a value which is calculated in direct proportion to a signal produced by an actuator (not shown) on the hand controller 112 indicative of an amount of pressure the operator exerts by squeezing the actuator to actuate the gripper jaws 220 to close).

To calculate the configuration variables, it will first be recalled that the end effector rotation matrix $R_{EENEW}$ is a 3×3 matrix:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the last column of $R_{EENEw}$ is the z-axis of the end effector reference frame written relative to the fixed slave reference frame $x_v$, $y_v$, and $z_v$. The values $\vartheta_{dist}$, $\delta_{dist}$, and $\gamma$ associated with the distal segment 702 may be calculated according to the relations:

$$\theta_{dist} = \frac{\pi}{2} - \text{atan2}\left(\sqrt{z_{2x}^2 + z_{2y}^2}, z_{2z}\right) \quad \text{Eqn 2}$$

$$\delta_{dist} = -\text{atan2}(z_{2y}, z_{2x}). \quad \text{Eqn 3}$$

If $|\delta_{dist}| > \frac{\pi}{2}$:

$$\gamma = \text{atan2}(-y_{2z}, -x_{2z}) - \delta_{dist} + \pi \quad \text{Eqn 4a}$$

else $$\gamma = \text{atan2}(y_{2z}, -x_{2z}) - \delta_{dist} \quad \text{Eqn 4b}$$

The third position 706 may then be written in terms of a vector $\bar{p}_{3/v}$ from the fixed slave reference position 652 to the third position. Similarly a vector $\bar{p}_{4/3}$ may be defined from the third position 706 to the fourth position 710 and a vector $\bar{p}_{5/4}$ may be defined from the fourth position 710 to the end effector position 660. These values can then be used to compute the location of third position 706 relative to the fixed slave reference position 652 by subtracting the vectors $\bar{p}_{4/3}$ and $\bar{p}_{5/4}$ from the end effector position vector $\vec{P}_{EENEW}$:

$$\bar{p}_{3/v} = \vec{P}_{EENEW} - \bar{p}_{4/3} - \bar{p}_{5/4}, \quad \text{Eqn 5}$$

where:

$$\bar{p}_{4/3} \cdot \bar{i} = \frac{-L_2 \cos\delta_{dist}(\sin\theta_{dist} - 1)}{\frac{\pi}{2} - \theta_{dist}} \quad \text{Eqn 6a}$$

$$\bar{p}_{4/3} \cdot \bar{j} = \frac{L_2 \sin\delta_{dist}(\sin\theta_{dist} - 1)}{\frac{\pi}{2} - \theta_{dist}} \quad \text{Eqn 6b}$$

$$\bar{p}_{4/3} \cdot \bar{k} = \frac{L_2 \cos(\theta_{dist})}{\frac{\pi}{2} - \theta_{dist}} \quad \text{Eqn 6c}$$

$$\bar{p}_{5/4} \cdot \bar{i} = L_3 \cos(\delta_{dist})\cos(\theta_{dist}) \quad \text{Eqn 7a}$$

$$\bar{p}_{5/4} \cdot \bar{j} = -L_3 \sin(\delta_{dist})\cos(\theta_{dist}) \quad \text{Eqn 7b}$$

$$\bar{p}_{5/4} \cdot \bar{k} = L_3 \sin(\theta_{dist}), \quad \text{Eqn 7c}$$

where $\bar{i}$ is a unit vector in the x direction, $\bar{j}$ is a unit vector in the y direction, and $\bar{k}$ is a unit vector in the z direction.

The vector $\bar{p}_{3/v}$ from the fixed slave reference position 652 to the third position 706 may then be used to find the configuration variables $\delta_{prox}$ and $\vartheta_{prox}$ for the s-segment 700. The angle $\delta_{prox}$ is calculated by solving the following two equations for $\vartheta_{prox}$:

$$\bar{p}_{3/v} \cdot \bar{i} = \frac{-L_1 \cos\delta_{prox}(\sin\theta_{prox} - 1)}{\frac{\pi}{2} - \theta_{prox}} \quad \text{Eqn 8a}$$

$$\bar{p}_{3/v} \cdot \bar{j} = \frac{L_1 \sin\delta_{prox}(\sin\theta_{prox} - 1)}{\frac{\pi}{2} - \theta_{prox}}. \quad \text{Eqn 8b}$$

Taking a ratio of Eqn 8b and Eqn 8a yields:

$$\delta_{prox} = \text{atan2}(-\bar{p}_{3/v} \cdot \bar{j}, \bar{p}_{3/v} \cdot \bar{i}), \quad \text{Eqn 9}$$

where $\bar{i}$ and $\bar{j}$ are unit vectors in the x and y directions respectively. A closed form solution cannot be found for $\vartheta_{prox}$, and accordingly $\vartheta_{prox}$ must be found using a numerical equation solution to either of equations Eqn 8a or Eqn 8b. For example, a Newton-Raphson method may be employed, which iteratively approximates successively better roots of a real-valued function. The Newton-Raphson method can be implemented using the following equations:

$$f(\theta_{prox}) = \frac{L_1}{\frac{\pi}{2} - \theta_{prox}} \cos\delta_{prox}(1 - \sin\theta_{prox}) - \bar{p}_{3/v} \cdot \bar{i} = 0, \quad \text{Eqn 10}$$

where $\bar{i}$ is the unit vector in the x direction. The equation Eqn 10 is Eqn 8a rewritten in the form $f(\vartheta_{prox})=0$. The Newton-Raphson method tends to converge very quickly because in the range $0 < \vartheta_{prox} < \pi$, the function has a large radius of curvature and has no local stationary points. Following the Newton-Raphson method, successive improved estimates of $\vartheta_{prox}$ can be made iteratively to satisfy equation Eqn 10 using the following relationship:

$$\theta_{n+1} = \theta_n - \frac{f(\theta_n)}{f'(\theta_n)} \quad \text{Eqn 11}$$

Finally, upon determination of $\vartheta_{prox}$, the following equation can be used to find $q_{ins}$:

$$q_{ins} = -\bar{p}_{3/v} \cdot \bar{k} - \frac{L_1 \cos\theta_{prox}}{\frac{\pi}{2} - \theta_{prox}}, \quad \text{Eqn 12}$$

where $\bar{k}$ is the unit vector in the z direction and $\bar{p}_{3/v} \cdot \bar{k}$ is the dot product of the vector $\bar{p}_{3/v}$ and the unit vector $\bar{k}$.

The above configuration variables calculated for the end effector position and orientation signals $\vec{P}_{EENEW}$ and $R_{EENEW}$ at block 606 or $\vec{P}_{EEPREV}$ and $R_{EEPREV}$ at block 614 of the processes 602 and 630. The configuration variables generally define a pose of the manipulator 210 required to position the end effector 212 at the desired location and orientation in end effector workspace. Configuration variables are produced for each end effector 212 and 218 of the respective right and left side tools 208 and 212. Two sets of configuration variables referred to as left and right configuration variables respectively are thus produced and transmitted by the motion control interface 258 to the instrument processor circuit 130 and used by the microprocessor 280 to generate drive control signals for spatially positioning the manipulator 210 and end effector 212 of the tool 208 in the surgical workspace.

Figure 10:
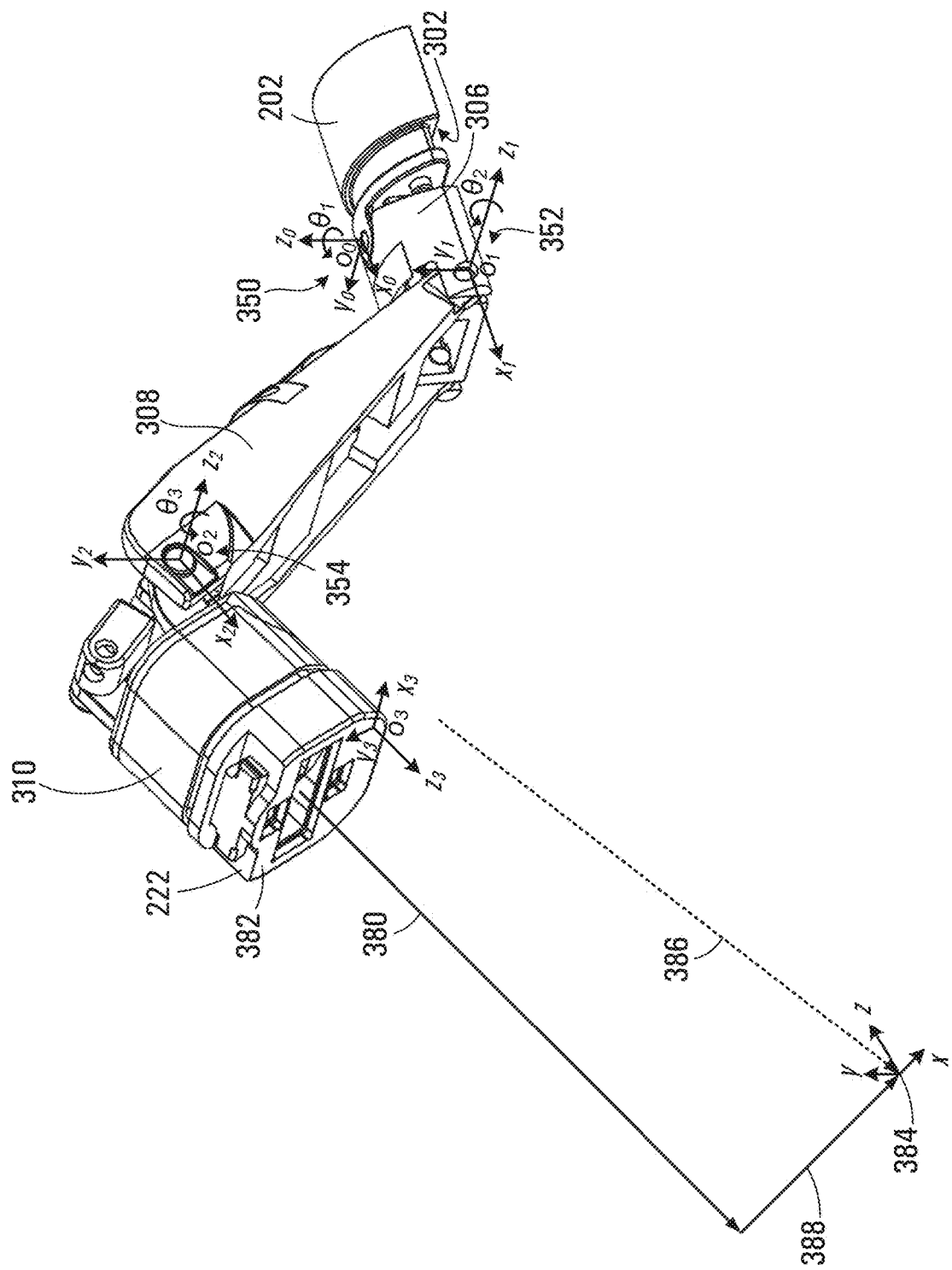
FIG. 10 is a perspective view of a camera and plurality of connected linkages of the robotic surgery system shown in FIG. 1 according to some embodiments.

The values of the vector $\vec{P}_{EENEW}$ and rotation matrix $R_{EENEW}$ calculated as described above and stored in stores 330 and 332 of the current buffer 320 of the workstation memory 252 define the location (x, y, z) of the end effector 212 of the tools 208 within the surgical workspace relative to the fixed slave reference frame $x_v$, $y_v$, $z_v$ (shown in FIG. 6). These values provide a target for orienting the camera 222 by actuating the plurality of connected linkages 300 shown in FIG. 3 to orient the camera 222 toward the location of the end effector 212. Referring to FIG. 10, in some embodiments, the camera 222 and plurality of connected linkages 300 are shown with each the linkages 306, 308, and 310 having a respective coordinate frames $O_0$, $O_1$, and $O_2$ disposed at the respective revolute joints 350, 352, and 354 and the coordinate frame $O_3$ at a face of the camera 222. The location and orientation of the camera 222 (frame $O_3$) may be expressed with respect to a base frame $O_0$ as:

$$T_{03} = A_{01}(\theta_1) A_{12}(\theta_2) A_{23}(\theta_3) \qquad \text{Eqn 13}$$

The transformation matrix $T_{03}$ is a transformation matrix from the distal end 302 of the insertion tube 202 to the camera 222, where:

$$A_{01} = \begin{bmatrix} c_1 & 0 & s_1 & a_1 c_1 \\ s_1 & 0 & -c_1 & a_1 s_1 \\ 0 & 1 & 0 & 0 \\ 0 & 0 & 0 & 1 \end{bmatrix}$$

$$A_{12} = \begin{bmatrix} c_2 & -s_2 & 0 & a_2 c_2 \\ s_2 & c_2 & 0 & a_2 s_2 \\ 0 & 0 & 1 & 0 \\ 0 & 0 & 0 & 1 \end{bmatrix}$$

$$A_{23} = \begin{bmatrix} c_3 & 0 & s_3 & a_3 c_3 \\ s_3 & 0 & -c_3 & a_3 s_3 \\ 0 & 1 & 0 & 0 \\ 0 & 0 & 0 & 1 \end{bmatrix}$$

and where:

$o_0, x_0, y_0, z_0$ coordinate frame of the revolute joint 350;
$o_1, x_1, y_1, z_1$ coordinate frame of the revolute joint 352;
$o_2, x_2, y_2, z_2$ coordinate frame of the revolute joint 354;
$o_3, x_3, y_3, z_3$ coordinate frame of the camera 222;
$a_1$ perpendicular distance from $z_0$ to $z_1$ (the length of the panning linkage 306);
$a_2$ perpendicular distance from $z_1$ to $z_2$ (the length of link elevating linkage 308);
$a_3$ perpendicular distance from $z_2$ to $z_3$ (the length of the camera tilt linkage 310);
$s_i$ sin $\vartheta_i$ (i=1, 2, 3);
$c_i$ cos $\vartheta_i$ (1=1, 2, 3);
$s_{23}$ sin $(\vartheta_2 + \vartheta_3)$;
$c_{23}$ cos $(\vartheta_2 + \vartheta_3)$;
$\vartheta_1$ angular displacement of the panning linkage 306;
$\vartheta_2$ angular displacement of the elevating linkage 308;
$\vartheta_3$ angular displacement of the tilt linkage 310;
$A_{i-1,i}$ coordinate transformation matrix from frame $o_i$ to frame $o_{i-1}$
$T_{o3}$ coordinate transformation from the camera 222 frame $O_3$ to the base frame $O_0$.

In one embodiment an orientation vector 380 is defined that is directed outwardly and perpendicular to a front face 382 of the camera 222. The orientation vector 380 is thus aligned with the tilt linkage 310 and provides an indication of the current orientation of the camera 222. A set of axes 384 represent the location information defining the location of the tool with respect to a body cavity frame of reference and act as a target location for orienting the vector 380 associated with the camera 222. In FIG. 10, the desired new orientation is represented by a vector 386, which provides a target for aligning the tilt linkage 310 of the camera 222. A difference vector 388, indicative of the required movement of the kinematic system to direct front face 382 of the camera 222 toward the target set of axes 384, may be computed and used as an input to the transformation of Eqn 13 to compute required movements of each of the respective revolute joints 350, 352, and 354 to move the linkages 306, 308, and 310 for orienting the camera 222.

While specific embodiments have been described and illustrated, such embodiments should be considered illustrative of the disclosure only and not as limiting the disclosure as construed in accordance with the accompanying claims.

What is claimed is:

1. In a surgical robotic system, a method for positioning a camera to capture images inside a body cavity of a patient during a medical procedure, the method comprising:
   receiving location information of at least one tool at a controller of the surgical robotic system performing the medical procedure, the location information defining a location of the at least one tool with respect to a body cavity frame of reference;
   receiving at the controller an align command signal configured to cause the controller to move the camera based on the location information of the at least one tool; and
   in response to receiving the align command signal at the controller, positioning the camera within the body cavity frame of reference to align a field of view of the camera with the location of the at least one tool such that the camera captures images of the at least one tool for display to an operator of the surgical robotic system.

2. The method of claim 1 wherein movement of the at least one tool within the body cavity is caused by movement signals produced by the controller based on kinematic calculations and wherein receiving location information comprises using results of the kinematic calculations to determine the location of the at least one tool.

3. The method of claim 1 further comprising receiving location signals at the controller, the location signals being indicative of an actual location of the at least one tool within the body cavity frame of reference.

4. The method of claim 1 wherein causing the controller to produce positioning signals comprises causing the controller to produce positioning signals operable to cause the camera to be positioned such that the field of view of the camera is disposed to cause a reference point associated with the at least one tool to be centered within the captured images.

5. The method of claim 4 wherein the reference point comprises a point on the at least one tool proximate a distal end of the at least one tool.

6. The method of claim 4 wherein receiving location information comprises receiving location information defining locations of a plurality of tools with respect to a body cavity frame of reference, and wherein the reference point comprises a point disposed in-between respective distal ends of the plurality of tools.

7. The method of claim 5 further comprising receiving operator input of a desired offset between the reference point and a center of the field of view of the camera and wherein causing the controller to produce positioning signals comprises causing the controller to produce positioning signals operable to cause the camera to be positioned such that the field of view of the camera is disposed offset from the reference point by the desired offset within the captured images.

8. The method of claim 1 further comprising, while the align command signal is being received at the controller and in response to receiving operator input from an input device configured to generate input signals for controlling movement of the at least one tool, causing the controller to continue to produce movement signals for causing movement of the at least one tool while simultaneously producing camera positioning signals operable to cause the camera to follow the at least one tool within the body cavity frame of reference.

9. The method of claim 1 wherein receiving the align command signal comprises causing the controller to determine whether a camera align control has been activated by the operator.

10. The method of claim 9 wherein the camera align control comprises one or more of a finger actuated switch and a foot actuated switch.

11. The method of claim 1 wherein receiving the align command signal comprises causing the controller to determine whether at least one of:
  a pattern of movement of the at least one tool has been received at an input device configured to generate input signals for controlling movement of the at least one tool; and
  a pattern of movement of an end effector disposed at a distal tip of the at least one tool has been received from an input device configured to generate input signals for controlling movement of the end effector.

12. The method of claim 1 wherein receiving the align command signal comprises causing the controller to determine whether at least one of:
  a reference point associated with the at least one tool is disposed outside of a defined central region within the captured image; and
  a reference point associated with a currently active one of a plurality of tools is disposed outside of a defined central region within the captured image.

13. An apparatus for positioning a camera to capture images inside a body cavity of a patient during a medical procedure performed by a surgical robotic system, the apparatus comprising:
  a controller configured to receive location information of at least one tool, the location information defining a location of the at least one tool with respect to a body cavity frame of reference;
  the controller being further configured to receive an align command signal configured to cause the controller to move the camera based on the location information of the at least one tool; and
  the controller being further configured to, in response to receiving the align command signal, position the camera within the body cavity frame of reference to align a field of view of the camera with the location of the at least one tool such that the camera captures images of the at least one tool for display to an operator of the surgical robotic system.

14. The apparatus of claim 13 wherein movement of the at least one tool within the body cavity is caused by movement signals produced by the controller based on kinematic calculations and wherein the controller is configured to receive location information by using results of the kinematic calculations to determine the location of the at least one tool.

15. The apparatus of claim 13 wherein the controller is configured to receive location signals, the location signals being indicative of an actual location of the at least one tool within the body cavity frame of reference.

16. The apparatus of claim 13 wherein the controller is configured to produce positioning signals operable to cause the camera to be positioned such that the field of view of the camera is disposed to cause a reference point associated with the at least one tool to be centered within the captured images.

17. The apparatus of claim 16 wherein the reference point comprises a point on the at least one tool proximate a distal end of the at least one tool.

18. The apparatus of claim 16 wherein the controller is configured to receive location information defining locations of a plurality of tools with respect to a body cavity frame of reference, and wherein the reference point comprises a point disposed in-between respective distal ends of the plurality of tools.

19. The apparatus of claim 17 wherein the controller may be configured to receive operator input of a desired offset between the reference point and a center of the field of view of the camera and the controller may be further configured to cause the camera to be positioned such that the field of view of the camera is disposed offset from the reference point by the desired offset within the captured images.

20. The apparatus of claim 13 wherein, while the align command signal is being received at the controller and while receiving operator input from an input device configured to generate input signals for controlling movement of the at least one tool, the controller is configured to continue to produce movement signals for causing movement of the at least one tool while simultaneously producing camera positioning signals operable to cause the camera to follow the at least one tool within the body cavity frame of reference.

21. The apparatus of claim 13 wherein the align command signal is produced in response to determining that a camera align control has been activated by the operator.

22. The apparatus of claim 21 wherein the camera align control comprises one or more of a finger actuated switch and a foot actuated switch.

23. The apparatus of claim 13 wherein the align command signal is produced in response to the controller determining whether at least one of:
  a pattern of movement of the at least one tool has been received at an input device configured to generate input signals for controlling movement of the at least one tool; and
  a pattern of movement of an end effector disposed at a distal tip of the at least one tool has been received from an input device configured to generate input signals for controlling movement of the end effector.

24. The apparatus of claim 13 wherein the align command signal is produced by the controller when at least one of:
  a reference point associated with the at least one tool is disposed outside of a defined central region within the captured image; and
  a reference point associated with a currently active one of a plurality of tools is disposed outside of a defined central region within the captured image.

* * * * *